(12) United States Patent
Hopf et al.

(10) Patent No.: US 11,541,223 B2
(45) Date of Patent: Jan. 3, 2023

(54) PLUG VALVE FOR MEDICAL TECHNOLOGY

(71) Applicant: Hans-Juergen Hopf, Zirndorf (DE)

(72) Inventors: Michael Hopf, Zirndorf (DE); Norbert Kassai, Oberasbach (DE)

(73) Assignee: Hans-Juergen Hopf, Zirndorf (DE)

( * ) Notice: Subject to any disclaimer, the term of this patent is extended or adjusted under 35 U.S.C. 154(b) by 303 days.

(21) Appl. No.: 16/770,390

(22) PCT Filed: Dec. 3, 2018

(86) PCT No.: PCT/EP2018/083373
§ 371 (c)(1),
(2) Date: Jun. 5, 2020

(87) PCT Pub. No.: WO2019/110522
PCT Pub. Date: Jun. 13, 2019

(65) Prior Publication Data
US 2020/0384258 A1    Dec. 10, 2020

(30) Foreign Application Priority Data

Dec. 6, 2017   (DE) .......................... 102017129033.8

(51) Int. Cl.
*A61M 39/22* (2006.01)
*F16K 11/085* (2006.01)
(Continued)

(52) U.S. Cl.
CPC ......... *A61M 39/223* (2013.01); *F16K 5/0442* (2013.01); *F16K 11/085* (2013.01); *F16K 27/065* (2013.01)

(58) Field of Classification Search
CPC ................ A61M 39/223; A61M 39/22; A61M 2039/229; F16K 5/0407; F16K 5/04;
(Continued)

(56) References Cited

U.S. PATENT DOCUMENTS 3,276,472 A * 10/1966 Jinkens ................ A61M 39/223
604/83
3,783,900 A * 1/1974 Waldbillig .......... F16K 11/0853
251/309
(Continued)

FOREIGN PATENT DOCUMENTS

DE    102015119899 A1 *  5/2017  ......... A61M 39/223
GB       1218955 A    *  1/1971
(Continued)

*Primary Examiner* — David Colon-Morales
(74) *Attorney, Agent, or Firm* — Douglas Denninger

(57) ABSTRACT

A connection system for components through which a fluid is passed comprises an actuator and a main housing. The actuator has a cylindrical portion with an outer face. A handgrip is arranged at a first end of the cylindrical portion. In the region of a second end the cylindrical portion has a cavity, which is open towards the second end, and in the region of the second end there are arranged at least two gate-like passage openings for fluid connection. The main housing has a main body and at least two fluid passages arranged laterally on the main body. The main body has a cavity with an open first end, a base in the region of a closed second end, and at least two laterally arranged openings. A substantially cylindrical protrusion is arranged on the base of the main body and a peripheral shaping is arranged in the region of the second end of the actuator, which shaping at least partially surrounds the protrusion and thus forms a counter bearing for the second end of the actuator.

12 Claims, 1 Drawing Sheet

Figure 1:
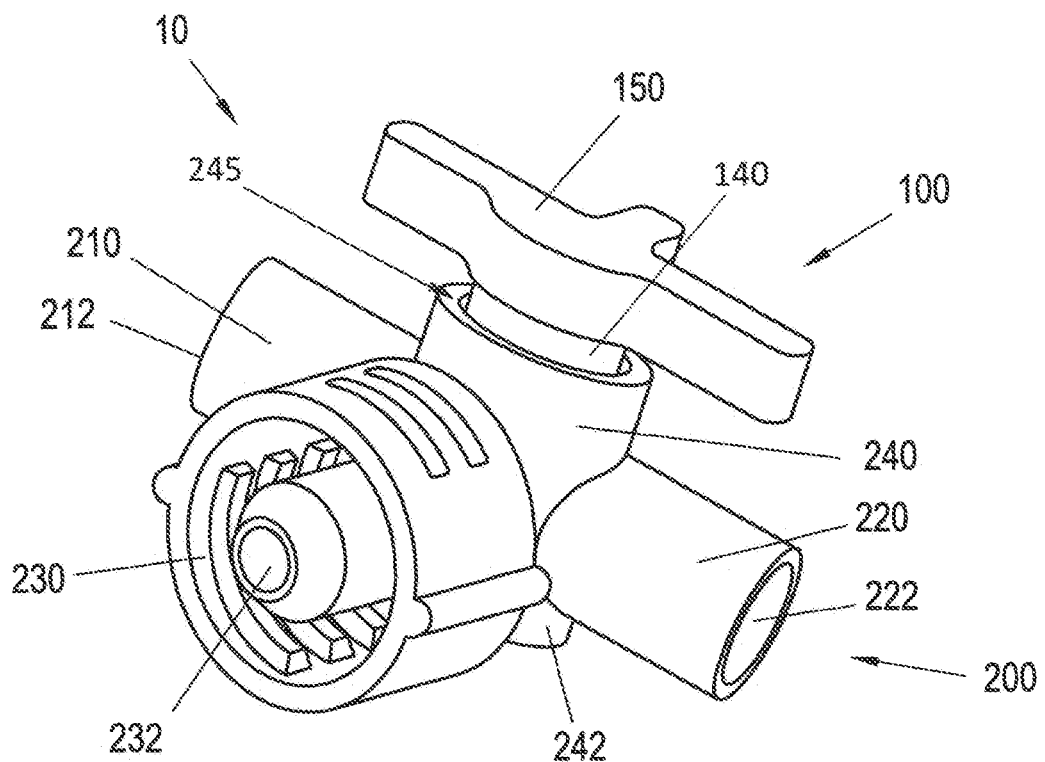

(51) Int. Cl.
*F16K 27/06* (2006.01)
*F16K 5/04* (2006.01)

(58) Field of Classification Search
CPC ...... F16K 5/0442; F16K 5/045; F16K 5/0485; F16K 11/085; F16K 11/0853; F16K 27/065; Y10S 251/904
See application file for complete search history.

(56) References Cited

U.S. PATENT DOCUMENTS

| | | | | |
|---|---|---|---|---|
| 4,890,817 A * | 1/1990 | Uri | ............. | F16K 27/065 251/312 |
| 2006/0033066 A1* | 2/2006 | Carrez | ............. | F16K 35/04 251/297 |
| 2008/0067462 A1* | 3/2008 | Miller | ............. | A61M 39/22 251/149.1 |
| 2013/0012915 A1* | 1/2013 | Hopf | ............. | A61M 39/00 604/500 |

FOREIGN PATENT DOCUMENTS

| | | | | | |
|---|---|---|---|---|---|
| GB | 1427821 A | * | 3/1976 | ......... | A61M 39/223 |
| WO | WO-2011119021 A1 | * | 9/2011 | ......... | A61M 39/10 |

* cited by examiner

PLUG VALVE FOR MEDICAL TECHNOLOGY

The present invention relates to a connection system, in particular with a plug valve, as used in medicine and/or medical technology, for example.

Connection systems in the above sense are known in the prior art. They are preferably used as connectors for enteral and/or parenteral applications. In at least some of these applications, higher pressures may also occur, for example in the range of up to 3 bar, and in individual cases even up to 10 bar. These connection systems should have a high degree of tightness in the blocked state, should allow a high flow rate and/or velocity in the open state, and should be easy to operate. For this purpose, prior art connection systems use relatively thick-walled designs of the plug, which are often supported at the base of the connection system. The disadvantages of these devices include the fact that they are not tight enough at higher pressures or are difficult to operate.

Proceeding from this prior art, it is the object of the present invention to at least partially overcome or mitigate the disadvantages of the prior art.

The object is achieved by a device according to claim 1. Preferred embodiments and modifications are the subject of the dependent claims.

A connection system according to the invention for components through which a fluid is passed for medicine and/or medical technology comprises an actuator and a main housing. The actuator has a cylindrical portion with an outer face. A handgrip is preferably arranged at a first end of the cylindrical portion. In the region of a second end the cylindrical portion has a cavity, which is open towards the second end, and in the region of the second end there are arranged at least two gate-like passage openings for a fluid connection. The main housing has a main body and at least two fluid passages arranged laterally on the main body. The main body has a cavity with an open first end, a base in the region of a second end, and at least two laterally arranged openings, which each produce a fluid connection to a corresponding one of the fluid passages. The cavity receives the cylindrical portion of the actuator rotatably through the open first end, and the inner diameter of the cavity corresponds to the outer diameter of the cylindrical portion of the actuator. The laterally arranged openings correspond to the passage openings of the actuator.

The invention is characterised in that a substantially cylindrical protrusion is arranged on the base of the main body and a peripheral shaping is arranged in the region of the second end of the actuator, which shaping at least partially surrounds the protrusion and thus forms a counter bearing for the second end of the actuator.

An actuator is an element designed to be arranged movably in a connection system. This movability should not affect the tightness of the connection system. An actuator according to the invention is suitable for being fitted into a main body. For this purpose, the actuator has a cylindrical portion with an outer face of which the diameter corresponds approximately to the inner diameter of a cavity in the main body, so that a good fit of the two elements—and thus a good movability and the tightness of the connection system—is ensured.

The handgrip, which is arranged at the first end of the actuator, can, for example, form a kind of crossbar, so that the actuator has a T-shaped appearance. The handgrip may also have three projections or branches, especially if the connection system is embodied as a three-way valve. The handgrip and the actuator may be formed in one piece. The handgrip may also consist only of a receptacle, for example in the form of a hex socket, into which a suitable handgrip element can be fitted.

The cylindrical portion of the actuator has, at least partially, a cavity so that the second end of the actuator is open. From this second end, passage openings extend, which are preferably gate-like, i.e. have the shape of an inverted U. Other shapes are also possible; the passage opening preferably has shapes which correspond to the openings in the main housing (said openings being arranged laterally on the main body). This ensures the largest possible diameter of the flow path continuously. The flow path comprises the fluid passages of the main body, their openings and the passage openings of the actuator. To enable the actuator to withstand higher fluid pressure as well, the second end of the actuator is supported, more specifically by a substantially cylindrical protrusion or pin at the base of the main body. In order to ensure that only a small amount of friction occurs at this location as well, a peripheral shaping is arranged in the region of the second end of the actuator and at least partially surrounds the protrusion and thus forms a counter bearing for the second end of the actuator.

Due to this design of the connection system, in particular due to the introduction and the special embodiment of the counter bearing, a connection system according to the invention achieves a high degree of tightness, even at higher pressure, and still has low friction and thus is easily handled. A large diameter of the entire flow path is given, so that a high flow rate and/or velocity in the open state is made possible.

In one specific embodiment of the connection system, the upper edge of the protrusion at the base of the main body is not higher than the lower edge of one of the fluid passages of the main body.

The fact that the upper edge of the protrusion, in relation to the base of the main body, is not higher than the lower edge of one of the fluid passages ensures a large diameter of the flow path continuously—i.e. also within the passage through the actuator. This advantageously further improves the flow through the entire connection system.

In some embodiments the protrusion has a cavity.

This not only has a positive effect on the flow of the fluid in the connection system, but also results in material savings. The cavity of the protrusion can face outwards or—preferably—inwards.

In some embodiments the protrusion has apertures. This is for embodiments in which the cavity of the protrusion faces inwards.

This is advantageous both for those embodiments in which the protrusion is solid and for those in which the protrusion has a cavity; this is because the flow rate is improved as a result of this as well. If the protrusion is solid, then these apertures are designed as a slot; in the case of three or more openings as a branched slot.

The upper edge of the protrusion is preferably round or bevelled. The peripheral shaping of the actuator, which corresponds to the protrusion, is also bevelled or rounded.

In some embodiments the fluid passage or its lateral surface has an internal thread, an external thread or another suitable connection structure in the region of its outer opening in order to act as a connection point for a component through which a fluid is passed, in particular for medicine and/or medical technology. In many cases, the fluid passage or its lateral surface is designed to fit together with, for example, a Luer connection and/or a connection according to ENFit™ (in particular according to ISO 80369-3).

In some embodiments, when the cylindrical portion of the actuator is arranged in the main body of the main housing, a gap remains between the second end of the actuator and the base of the cavity, so that an annular clearance is formed.

The fact that the second end of the cylindrical portion of the actuator is spaced apart from the base of the cavity results advantageously in the creation of an annular clearance through which the fluid can flow, thus further improving the flow rate. This embodiment also leads to a further reduction in friction between the actuator and the main body.

In some embodiments, the cylindrical portion of the actuator has an annular formation and the main body of the main housing has a radially peripheral indentation, so that when the cylindrical portion of the actuator is arranged in the main body of the main housing, the annular formation latches into the radially peripheral indentation.

This offers the advantage of an improved tightness of the connection system. Furthermore, the actuator is protected against falling out or being pressed out of the main body at high pressure. These embodiments are particularly suitable even for higher pressures. There may also be a number of annular formations and correspondingly a number of radially peripheral indentations.

In one specific embodiment, the cylindrical portion has, in the region of a first end, a further cavity, which is separated from the cavity.

This has the advantages of saving material and increasing the elasticity of the actuator.

In one specific embodiment, in the region of the second end of the cylindrical portion, the connection system has, between the passage openings, a protrusion and/or recess extending horizontally or vertically. This corresponds to a recess and/or protrusion of the pin. This makes it particularly easy for a valve to latch into its intended or preferred positions with sensory feedback.

In some embodiments the connection system has the following combinations of the number of openings of the main body and the number of openings of the cylindrical portion: 2 and 2, or 3 and 2, or 3 and 3, or 4 and 2, or 4 and 3, or 4 and 4.

In some embodiments the gate-like passage openings of the actuator have a semi-circular, in particular U-shaped, rectangular or triangular portion. The passage openings may also be hexagonal etc. or asymmetrical. Preferably, the shapes of the passage openings are adapted to the shapes of the openings of the fluid passages in the main body.

In some embodiments the surfaces of the connection system that come into contact with the fluid are made of an amorphous copolyester, at least in part.

In some embodiments in addition to the copolyester, other materials are used, which are selected from a group comprising thermosets and thermoplastics and in particular polyphenylene sulphide, polypropylene, poly-1-butene, 10 polyvinyl chloride, polyvinylidene chloride, polymethyl methacrylate, polyacrylonitrile, polystyrene, polysulphone, polyacetal, polyvinyl alcohol, polyvinyl acetate, ionomers, fluoroplastic, polyethylene, polyamide, in particular a partially aromatic polyamide, polycarbonate, polyester, polyphenylene oxide, polysulphone, polyvinyl acetal, polyurethane, and chlorinated polyether, cellulose nitrate, cellulose acetate, cellulose ether, phenolic resin, urea resin, thiourea resin, melamine resin, alkyl resin, allyl resin, silicone, polyimide, polybenzimidazole, epoxy resin, casein plastic, crosslinked polyurethane, unsaturated polyester resin, antimicrobial or antiseptic materials such as highly porous silver, silver prepared ion-free, silver compounds and in particular microsilver, metal ion-releasing compounds, and/or combinations thereof.

A connection system according to the invention is preferably used for medical technology.

The invention will be explained hereinafter on the basis of various embodiments, although it is noted that this example includes modifications or additions as are immediately clear to the person skilled in the art. Furthermore, this preferred exemplary embodiment does not constitute a limitation of the invention in the sense that modifications and additions lie within the scope of the present invention.

Figure 2:
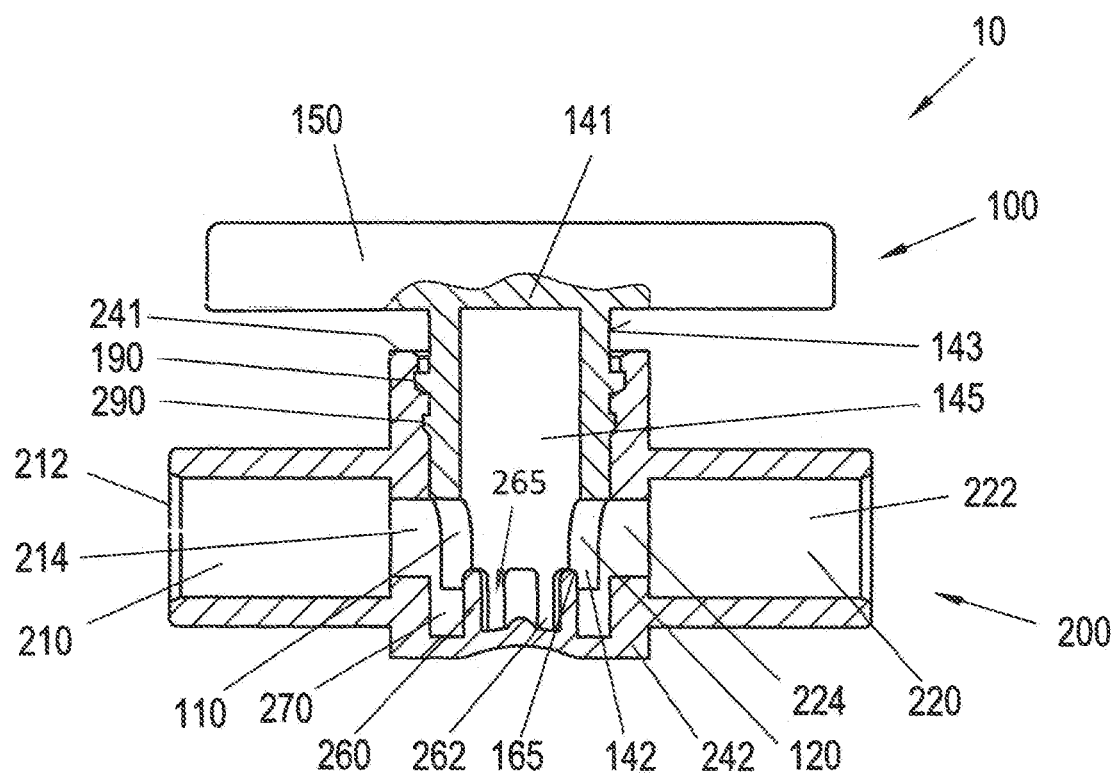

In the drawings:

FIG. 1: shows a perspective view of a connection system according to the invention;

FIG. 2: shows a sectional view through a connection system according to the invention.

FIG. 1 shows a connection system 10 in which the cylindrical portion 140 of the actuator 100 is arranged in the main body 240 of the main housing 200. The cylindrical portion 140 of the actuator 100 is therefore only partially visible. At the first end 141 of the cylindrical portion 140, there is arranged a handgrip 150. In the middle of the main housing 200, the main body 240 is visible with an open first end 241 and a closed second end 242. Furthermore lateral surfaces of the fluid passages 210, 220, 230 and their outer openings 212, 222, 232 are visible.

The way in which the actuator 100 interacts with the main housing 200 is particularly clear from the sectional view in FIG. 2. The flow path extends horizontally from the outer openings 212, 222, through the fluid passages 210, 220 of the main housing 200, through the gate-like passage openings 110, 120 of the actuator 100 and through a part of the cavity 145 of the actuator 100. It is clearly visible that the shape of the gate-like passage openings 110, 120 corresponds with the openings 214, 224 in the wall of the main body 240. The protrusion 260 has a cavity 265 and apertures 262. The upper edge of the protrusion 260 is not higher than the lower edge of one of the fluid passages 210, 220. These embodiments interact in such a way that, in the embodiment shown, a fluid can flow through the entire flow path quite freely. The second end 142 of the actuator 100 is spaced apart from the base of the main housing 200 so that a clearance 270 is formed, through which the fluid can also flow. The protrusion 260 and the corresponding peripheral shaping 165 are rounded. The small contact area of these elements helps to reduce the friction between the actuator 100 and the main housing 200. Above the gate-like passage openings 110, 120, two radially peripheral indentations 290 are arranged on the main body 240 and correspond to formations 190 which peripherally protrude from the outer face 143 of the actuator 100. These elements increase the tightness of the connection system 10 so that no fluid can escape even at higher pressures. At the same time, this further contributes to reducing friction, since there is thus no need for an extremely tight fit between the outer face 143 of the actuator 100 and the body 240.

LIST OF REFERENCE SIGNS 10 connection system
100 actuator
110, 120 gate-like opening
140 cylindrical portion
141 first end
142 second end 143 outer face
145 cavity
147 further cavity
150 operating element, handgrip
160 end face
165 peripheral shaping
190 formation
200 main housing
210, 220, 230 fluid passage
212, 222, 232 outer opening
214, 224 opening
240 main body
241 first end of the main body
242 second end, base, of the main body
245 cavity of the main body
260 protrusion, (perforated) pin
262 aperture
265 cavity
270 clearance
290 radially peripheral indentation

The invention claimed is:

1. A connection system for components through which a fluid is passed, comprising
   an actuator having a cylindrical portion with an outer face, and having a handgrip arranged at a first end of the cylindrical portion,
   wherein in a region of a second end the cylindrical portion has a cavity, which is open towards the second end, and
   wherein in the region of the second end there are arranged at least two gate-like passage openings for a fluid connection, and
   a main housing, having a main body and at least two fluid passages arranged laterally on the main body, the main body having a main body cavity with an open first end, a base in the region of a closed second end, and at least two laterally arranged openings, which each produce a fluid connection to a corresponding one of the fluid passages,
   wherein the main body cavity receives the cylindrical portion of the actuator rotatably through the open first end, and an inner diameter of the main body cavity corresponds to an outer diameter of the cylindrical portion of the actuator,
   wherein the laterally arranged openings correspond to the passage openings of the actuator, and
   wherein a substantially cylindrical bearing pin is arranged on the base of the main body to support the second end of the actuator and a peripheral surface shaping is formed in the region of the second end of the actuator, which shaping at least partially surrounds the bearing pin and thus forms a counter bearing for the second end of the actuator, the shaping being in contact with the bearing pin, and wherein an upper edge of the bearing pin is not higher than a lower edge of one of the fluid passages.

2. The connection system according to claim 1, wherein the bearing pin has a bearing pin cavity.

3. The connection system according to claim 1, wherein the bearing pin has apertures.

4. The connection system according to claim 1, wherein the bearing pin and the corresponding peripheral shaping are at least partially bevelled or rounded.

5. The connection system according to claim 1, wherein each fluid passage of the main housing has an internal thread in the region of its outer opening in order to function as a connection point for the component through which the fluid is passed.

6. The connection system according to claim 1, wherein when the cylindrical portion of the actuator is arranged in the main body of the main housing, a gap remains between the second end of the actuator and the base of the main body cavity, so that an annular clearance is formed.

7. The connection system according to claim 1, wherein the cylindrical portion of the actuator has an annular formation and the main body of the main housing has a radially peripheral indentation so that, when the cylindrical portion of the actuator is arranged in the main body of the main housing, the annular formation latches into the radially peripheral indentation.

8. The connection system according to claim 1, wherein in the region of the second end of the cylindrical portion, between the passage openings, there is arranged a protrusion and/or a recess extending horizontally or vertically, which corresponds to a recess and/or protrusion of the bearing pin.

9. The connection system according to claim 1, wherein the connection system has the following combinations of the number of openings in the main body and the number of openings in the cylindrical portion of the actuator:
   2 and 2, or 3 and 2, or 3 and 3.

10. The connection system according to claim 1, wherein the gate-like passage openings of the actuator have a semicircular, U-shaped, rectangular or triangular portion.

11. The connection system according to claim 1, wherein the surfaces of the connection system which come into contact with the fluid are made of an amorphous copolyester, at least in part.

12. The connection system according to claim 11, wherein in addition to the copolyester, other materials are used, which are selected from a group comprising polyphenylene sulphide, polypropylene, poly-1-butene, 10 polyvinyl chloride, polyvinylidene chloride, polymethyl methacrylate, polyacrylonitrile, polystyrene, polysulphone, polyacetal, polyvinyl alcohol, polyvinyl acetate, ionomers, fluoroplastic, polyethylene, polyamide, a partially aromatic polyamide, polycarbonate, polyester, polyphenylene oxide, polysulphone, polyvinyl acetal, polyurethane, and chlorinated polyether, cellulose nitrate, cellulose acetate, cellulose ether, phenolic resin, urea resin, thiourea resin, melamine resin, alkyl resin, allyl resin, silicone, polyimide, polybenzimidazole, epoxy resin, casein plastic, crosslinked polyurethane, unsaturated polyester resin, antimicrobial or antiseptic materials, and/or combinations thereof.

\* \* \* \* \*